(12) United States Patent
Bodwalk

(10) Patent No.: US 6,526,991 B2
(45) Date of Patent: Mar. 4, 2003

(54) ORAL HYGIENE TRAVEL KIT

(76) Inventor: Mark Anthony Bodwalk, 6922 Newman Rd., Clifton, VA (US) 20124

( * ) Notice: Subject to any disclaimer, the term of this patent is extended or adjusted under 35 U.S.C. 154(b) by 137 days.

(21) Appl. No.: 09/749,764

(22) Filed: Dec. 28, 2000

(65) Prior Publication Data

US 2002/0100490 A1 Aug. 1, 2002

(51) Int. Cl.$^7$ ................................ A45D 44/18
(52) U.S. Cl. ................ 132/309; 132/311; 132/324; 132/328; 401/190; 206/581
(58) Field of Search ................... 132/286, 308, 132/309, 310, 311, 321, 324, 325, 328; 401/286, 190, 118, 27; 206/581, 235, 438, 63.5, 362.2, 368; 15/184

(56) References Cited

U.S. PATENT DOCUMENTS

| | | | |
|---|---|---|---|
| 1,357,285 A | 11/1920 | Glatt | |
| 1,386,806 A | 8/1921 | Schmerler | |
| 1,473,766 A | 11/1923 | Healy | |
| 1,488,810 A | 4/1924 | Fraser | |
| 1,492,836 A | 5/1924 | Decker | |
| 1,505,363 A | 8/1924 | Mather | |
| 1,642,620 A | 9/1927 | Merrill | |
| 1,716,617 A | 6/1929 | Brockelsby | |
| 1,733,114 A | 10/1929 | Brennan | |
| 1,780,066 A | 10/1930 | Christian | |
| 1,792,429 A | 2/1931 | Klinger | |
| 2,053,145 A | 9/1936 | Hamel | |
| 2,199,922 A | 5/1940 | McManis et al. | |
| 2,233,522 A | 3/1941 | Fickle | |
| 2,468,732 A | 5/1949 | Boulicault | |
| 2,640,488 A | * 6/1953 | Velodota | 132/308 |
| 3,406,694 A | 10/1968 | Odence | |
| 3,830,404 A | * 8/1974 | Frazer | 222/78 |
| 4,275,750 A | 6/1981 | Clark | |
| 4,428,389 A | * 1/1984 | Sanchez Cordero | 132/325 |
| 4,768,531 A | 9/1988 | Broussard | |
| 4,827,951 A | 5/1989 | Grussmark | |
| 4,919,156 A | * 4/1990 | Gipson | 132/309 |
| 4,957,125 A | 9/1990 | Yaneza | |
| 5,044,386 A | 9/1991 | Nelson | |
| 5,078,526 A | 1/1992 | Corona | |
| 5,117,848 A | 6/1992 | Huang | |
| 5,152,307 A | 10/1992 | Schlaszus | |
| 5,244,096 A | * 9/1993 | Stoner | 206/581 |
| 5,415,187 A | * 5/1995 | Heneveld | 132/325 |
| 5,622,195 A | 4/1997 | Lee | |
| 5,832,940 A | 11/1998 | Embry et al. | |
| 5,865,195 A | 2/1999 | Carter | |
| 6,253,773 B1 | * 7/2001 | Ingemann | 132/310 |

* cited by examiner

Primary Examiner—Kevin Shaver
Assistant Examiner—David Comstock
(74) Attorney, Agent, or Firm—Lawrence R. Franklin

(57) ABSTRACT

A portable kit for promoting oral hygiene includes a toothbrush, toothpaste, and dental floss compactly arranged in one portion of a housing which outwardly resembles a fountain pen. The kit may also include a canister of breath spray in another portion of the housing.

10 Claims, 7 Drawing Sheets

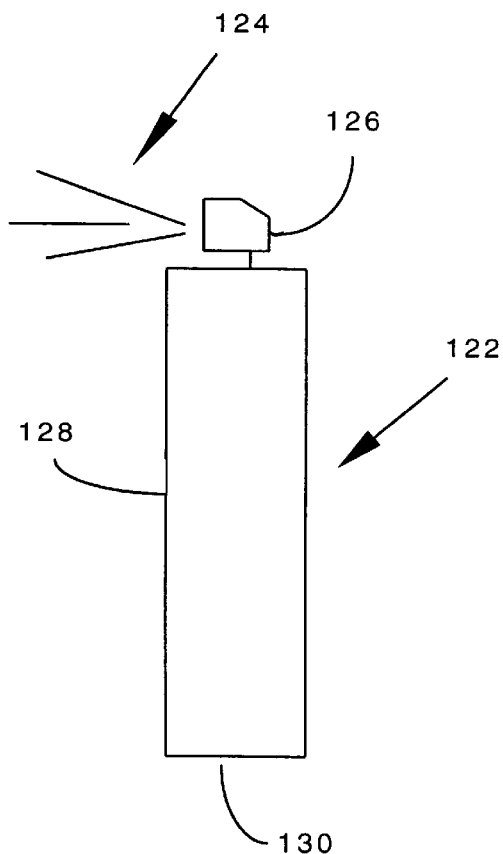
FIG. 14
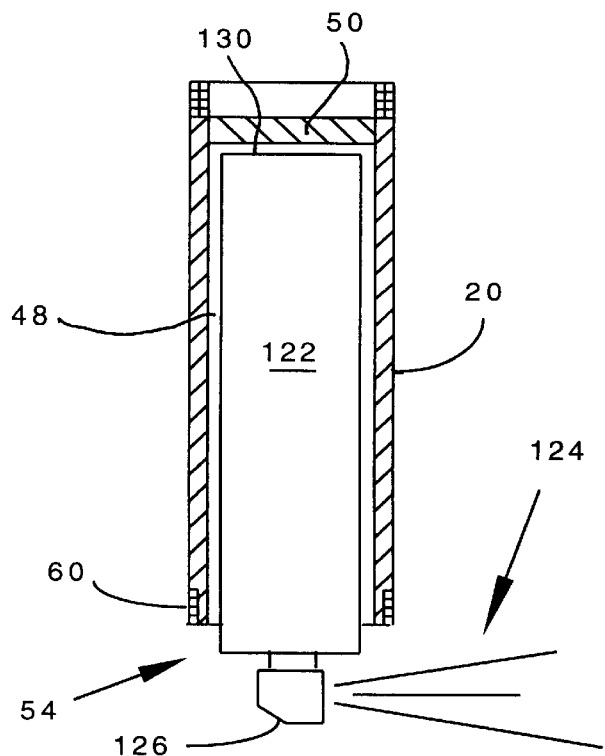
FIG. 15
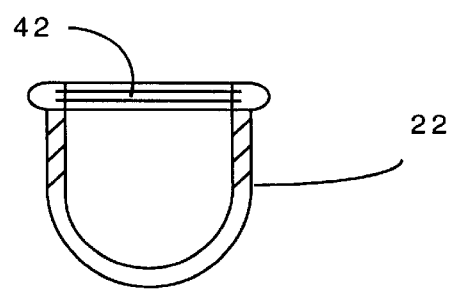

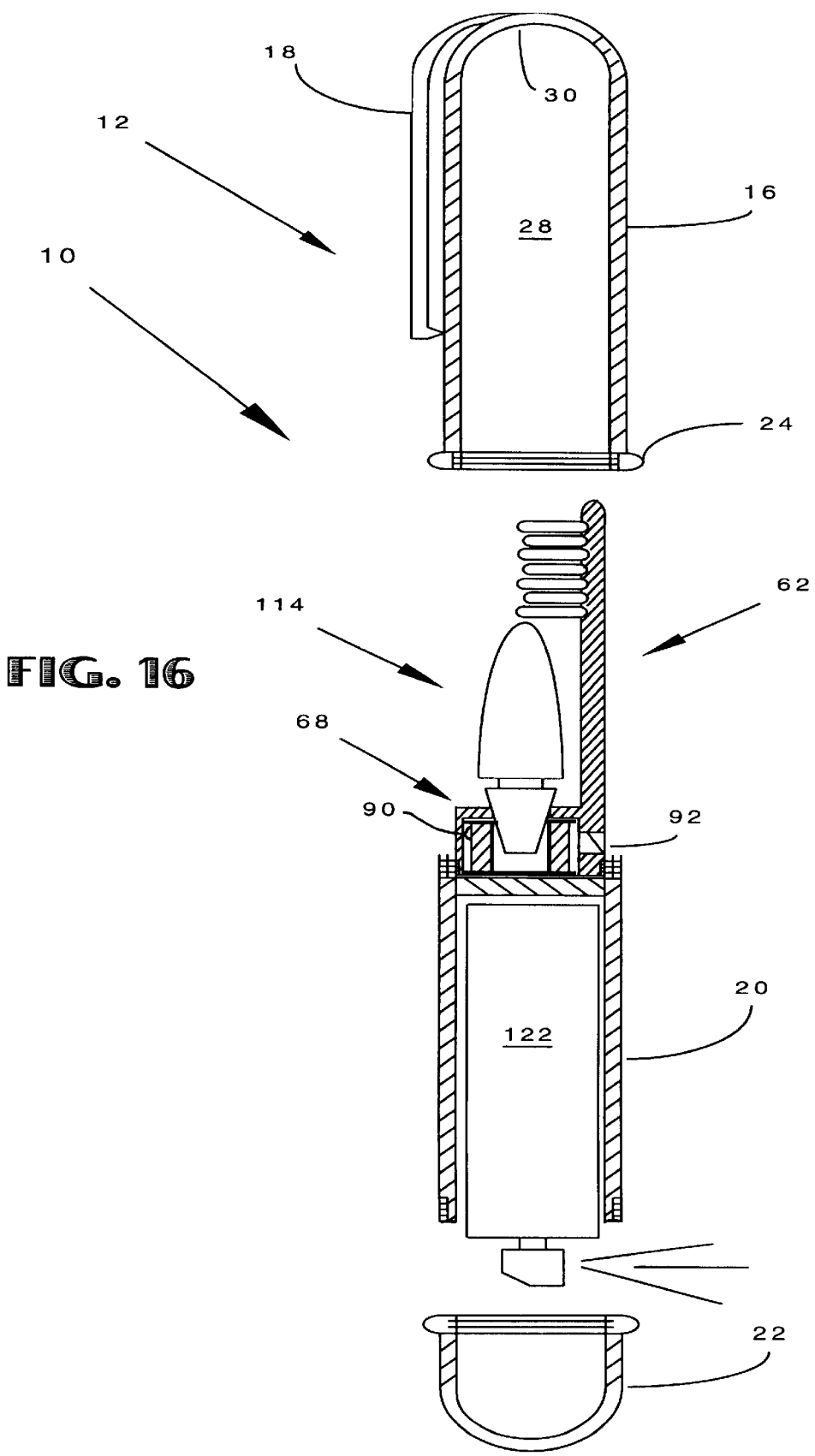

ORAL HYGIENE TRAVEL KIT

BACKGROUND OF THE INVENTION

1. Field of the Invention

This invention relates to a kit for promoting oral hygiene while away from home, for example, while at the office or when travelling. The kit comprises a toothbrush, toothpaste, dental floss, and breath spray contained in a housing which outwardly resembles a fountain pen.

2. Description of Related Art

Oral hygiene kits designed primarily for use outside the home which resemble a fountain pen are known.

The basic models combined a toothbrush and a dentifrice, such as toothpaste, in a fountain pen shaped housing. Representative are the following U.S. Patents: Glatt (U.S. Pat. No. 1,357,285), Schmerler (U.S. Pat. No. 1,386,806), Mather (U.S. Pat. No. 1,505,363), Brockelsby (U.S. Pat. No. 1,716,617), Christian (U.S. Pat. No. 1,780,066), Hamel (U.S. Pat. No. 2,053,145), Velodota (U.S. Pat. No. 2,640,488), Clark (U.S. Pat. No. 4,275,750), Broussard (U.S. Pat. No. 4,768,531), and Huang (U.S. Pat. No. 5,117,848). While sufficient for their intended purposes, as a group they are limited just to the brushing of teeth, only a part of complete oral hygiene.

Another group of inventors recognized that flossing is an important part of dental hygiene. This group provided a container (not disclosed as a simulated fountain pen) combining a dentifrice with a length of dental floss. Representative of this group are the following U.S. Patents: Fraser (U.S. Pat. No. 1,486,810), Decker (U.S. Pat. No. 1,492,836), Brennan (U.S. Pat. No. 1,733,114), Max Klinger (U.S. Pat. No. 1,792,429), and Grussmark (U.S. Pat. No. 4,827,951). These inventions did not meet the needs of travellers, inasmuch as a toothbrush had to be carried separately, and their containers were not as convenient nor as inconspicuous as a fountain pen.

A more complete kit combining a toothbrush, toothpaste, and dental floss received attention from another group of inventors: Healy (U.S. Pat. No. 1,473,766), Merrill (U.S. Pat. No. 1,642,620), McManis et al. (U.S. Pat. No. 2,199,922), Fickle (U.S. Pat. No. 2,233,522), Boulicault (U.S. Pat. No. 2,468,732), Gipson (U.S. Pat. No. 4,919,156), Yaneza (U.S. Pat. No. 4,957,125), Nelson (U.S. Pat. No. 5,044,386), Corona (U.S. Pat. No. 5,078,526), Embry et al. (U.S. Pat. No. 5,832,940), and Carter (U.S. Pat. No. 5,865,195). The embodiments in this group suffered from various problems, usually brought about by an attempt to limit the size of the "fountain pen". Corona, Embry et al., and Carter made no pretense at simulating a fountain pen, so the size and appearance of their inventions were disadvantageous. Most inventors aligned the toothbrush, toothpaste, and dental floss seriatim which resulted in overly large "fountain pens": Healy, Merrill, McManis et al., Fickle, Boulicault, Gipson, Yaneza, and Nelson. Healy and Nelson were alone in attempting a moderate degree of nesting elements, but they nested only two of their kit's components. Other problems find their roots in individual design considerations. In some, the bitter ends of the dental floss and their cutters were often exposed to contamination and damage: Healy, Merrill, Boulicault, Yaneza, and Corona. Nelson and Carter chose to hand-wind the dental floss on the toothbrush handle, where it was constantly exposed, an obvious disadvantage. Virtually all, Merrill, McManis et al., Fickle, Gipson, Yaneza, Nelson, Corona, Embry et al., and Carter hand-filled their toothpaste container, either a compartment in the fountain pen or a separate tube, a nuisance at best; at worst, the constant reusing of the container resulted in hardening of residual toothpaste which clogged the passageways, rendering the containers (which often meant the kit itself) unusable. Healy and Boulicault avoided this problem by using a dentifrice in a solid stick form. Nelson and Carter added a refillable compartment for mouthwash, which added to the size of the kit.

No one, to the inventor's knowledge, combined a toothbrush, toothpaste, dental floss, and breath spray in a single housing which outwardly resembled a fountain pen.

Other showings are worthy of note: Broussard and Lee (U.S. Pat. No. 5,622,195) replaced the dental floss with other items, namely, a flashlight and razor, respectively. Odence (U.S. Pat. No. 3,406,694) combined a hairbrush and hair spray in a single housing, not an oral hygiene kit nor a simulated fountain pen.

OBJECTS AND SUMMARY OF THE INVENTION

The present invention overcomes the difficulties described above by providing a toothbrush, toothpaste, dental floss, and a canister of breath spray in a simulated fountain pen. The fountain pen is of a reasonable size due to a better utilization of space within the fountain pen housing by nesting the toothbrush, toothpaste, and dental floss. Problems due to hand-refillable toothpaste containers, especially those built into the housing, and to hand-wound dental floss are avoided by using commercially available, individually packaged toothpaste tubes and dental floss spools which are easily replaceable. Contamination and damage thereof is obviated by housing them in protected areas sealed off from the external environment.

An object of the invention is to provide an oral hygiene kit comprising a fountain pen simulation housing a toothbrush, toothpaste, dental floss, and breath spray.

Another object of the invention is to nest the toothbrush, toothpaste, and dental floss in order to conserve space, thereby producing a smaller, more natural "fountain pen."

BRIEF DESCRIPTION OF THE DRAWINGS

The foregoing and other objects, aspects, uses, and advantages of the present invention will be more fully appreciated as the same becomes better understood from the following detailed description of the present invention when viewed in conjunction with the accompanying drawings, in which:

FIG. 14 is a side view of a canister of breath spray;

FIG. 15 is a side view, partially in cross-section, of the breath spray canister in combination with the body and lower cap of the fountain pen housing; and FIG. 16 is a side view, partially in cross-section, of the toothbrush, spool of oral floss, toothpaste, and canister of breath spray in combination with the fountain pen housing.

DETAILED DESCRIPTION OF THE PREFERRED EMBODIMENT

Figure 1:
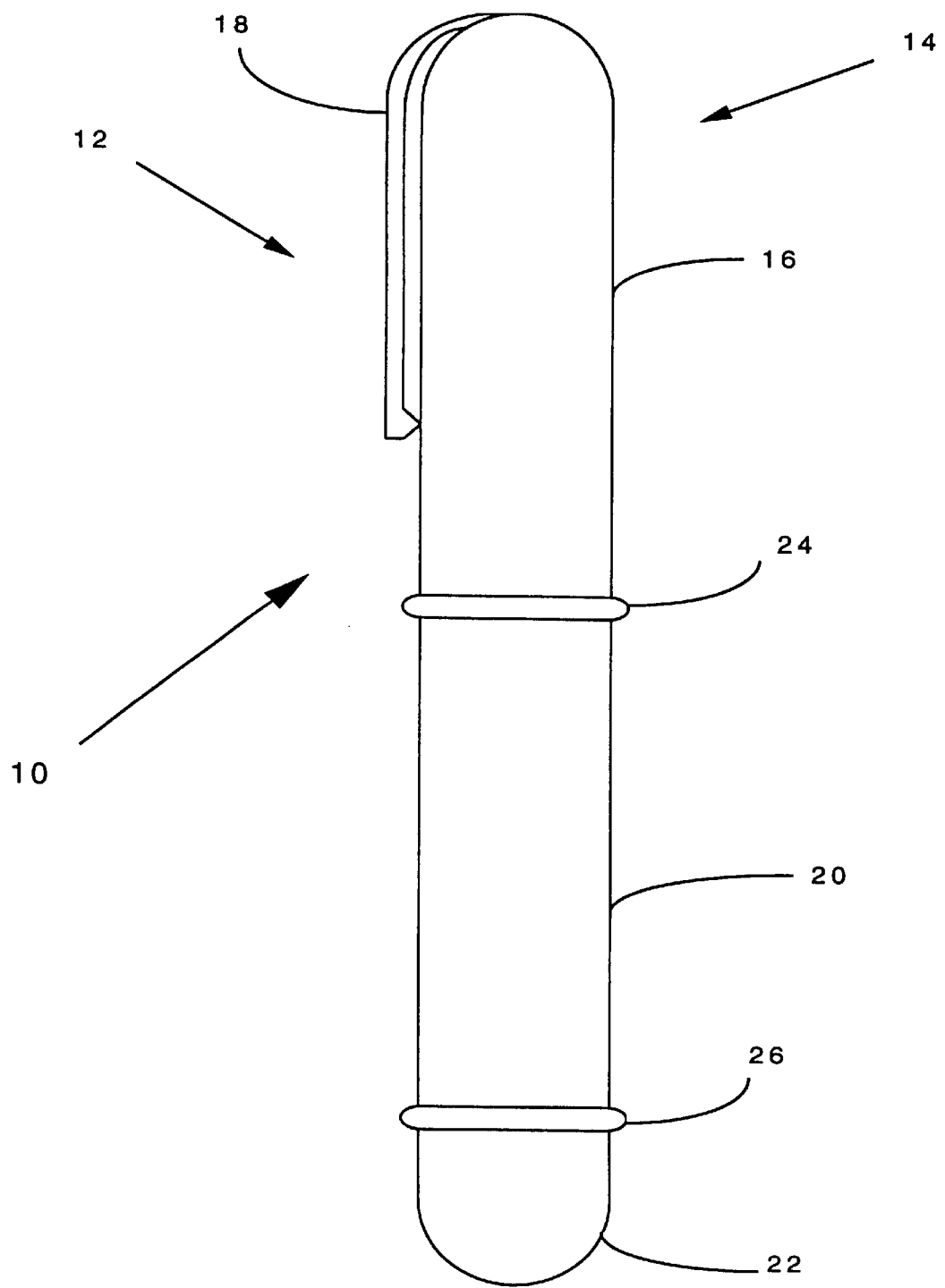
FIG. 1 is a front view of the oral hygiene kit having the appearance of a fountain pen which illustrates the preferred embodiment of the present invention.
Figure 2:
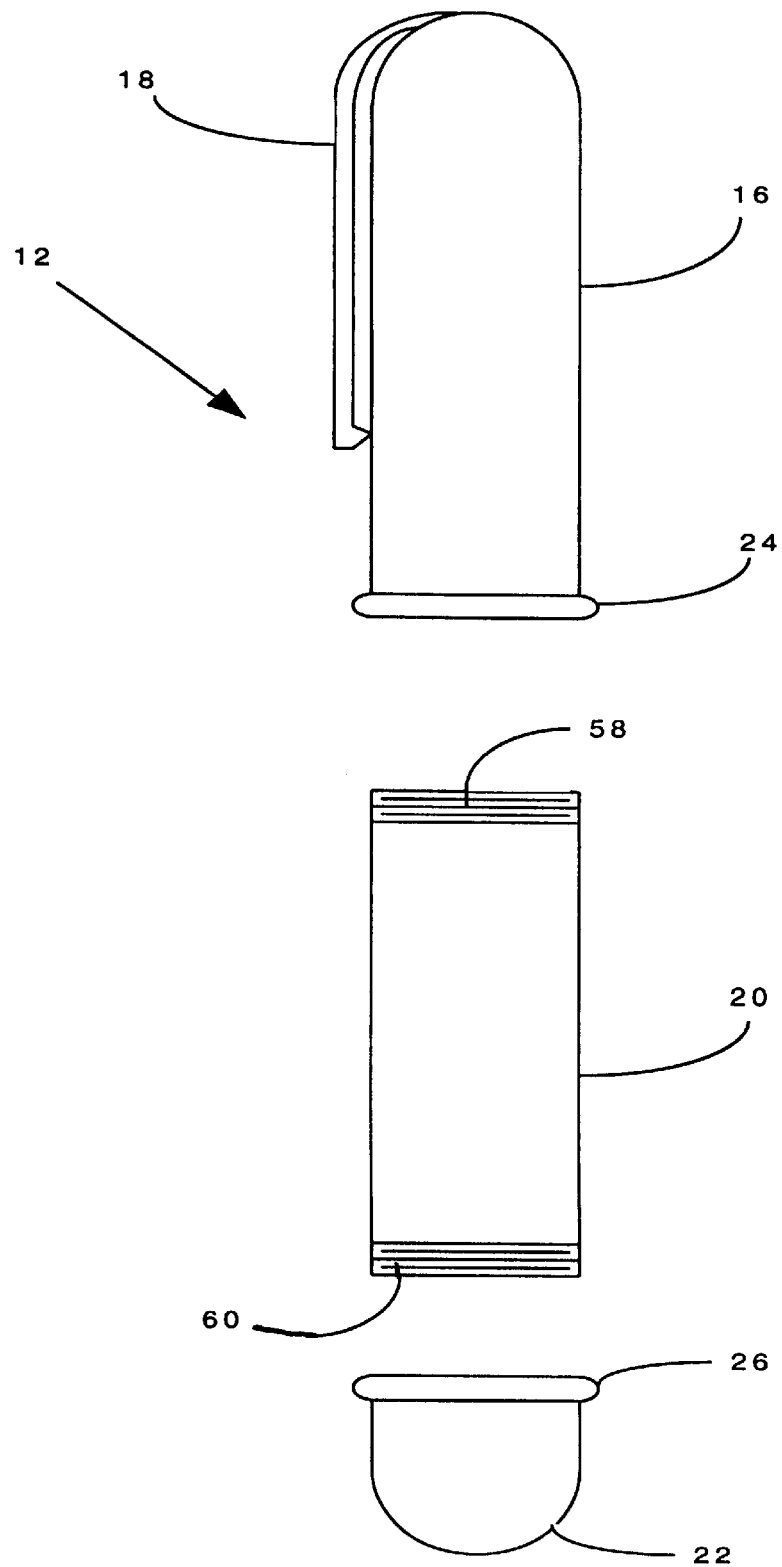
FIG. 2 is a front view of the fountain pen housing with the upper cap and lower cap separated from the body.
Figure 3:
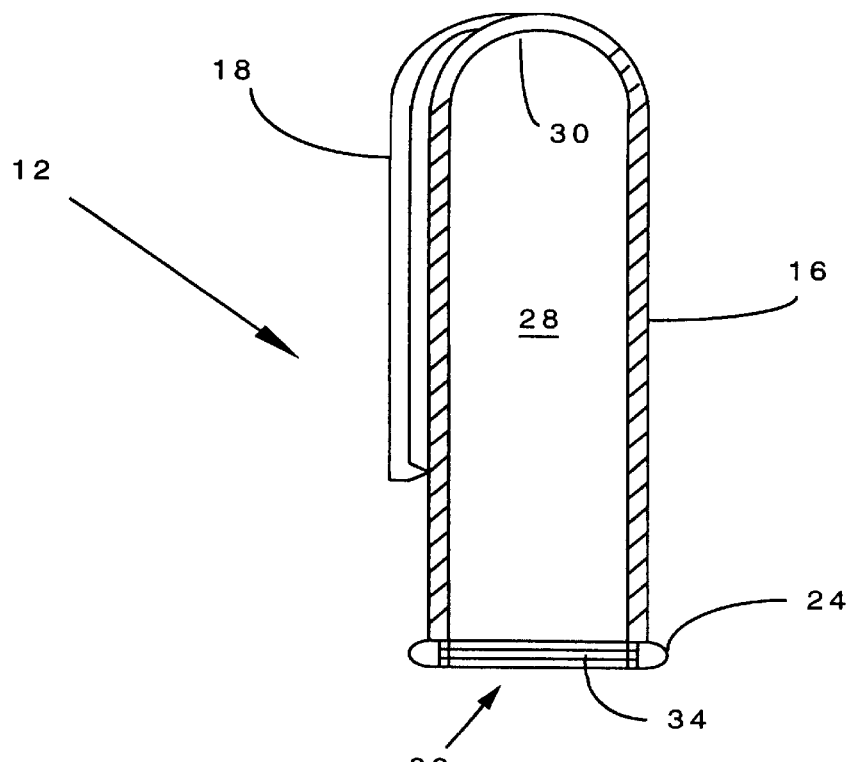
FIG. 3 is a cross-sectional view of the upper cap of the oral hygiene kit.
Figure 4:
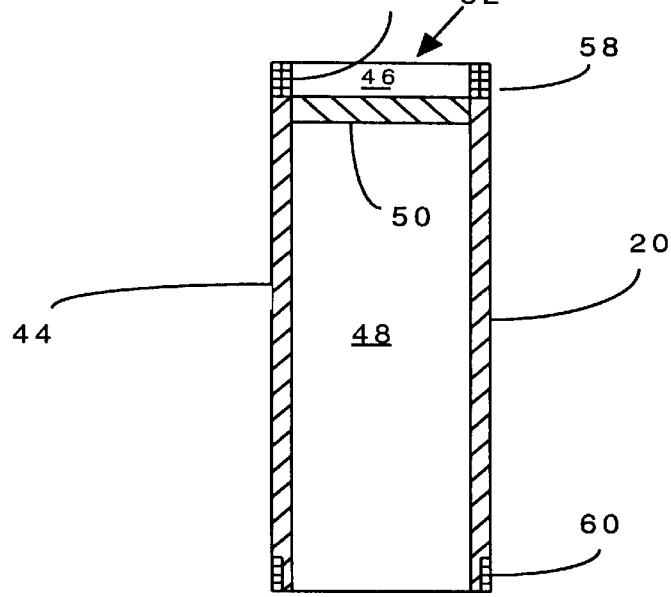
FIG. 4 is a cross-sectional view of the body of the oral hygiene kit.
Figure 5:
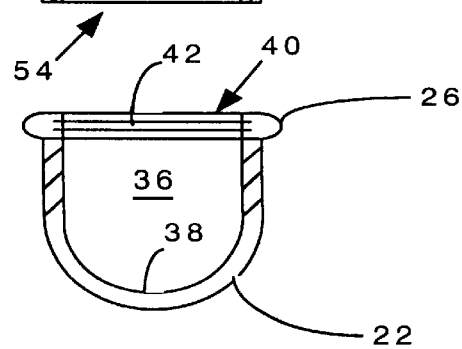
FIG. 5 is a cross-sectional view of the lower cap of the oral hygiene kit.

Referring to FIGS. 1–5, the inventive oral hygiene kit 10 comprises a housing 12 shown as simulating a fountain pen 14, its preferred outward appearance. Housing 12 comprises an upper cap 16 with a fountain pen type clasp 18 attached thereto, a body 20, and a lower cap 22. Upper cap 16, body 20, and lower cap 22 are constructed of any of the usual materials used for making fountain pens. Upper cap 16 and lower cap 22 each include a ferrule 24 and 26, respectively, typically made of silver, gold, or brass. As seen in FIG. 3, upper cap 16 comprises a hollow interior cavity 28 closed at the top 30 and open at the bottom 32. Upper cap 16 has internal threads 34 adjacent bottom opening 32; ferrule 24 surrounds opening 32 for aesthetic and functional purposes, inasmuch as it is both decorative and it reinforces upper cap 16 at its open end 32. Lower cap 22 (FIG. 5) is similarly constructed with a hollow interior cavity 36 closed at the bottom 38 and open at the top 40; lower cap 22 has internal threads 42 adjacent top opening 40 which is similarly reinforced by ferrule 26. Body 20 comprises a hollow cylinder 44 separated into two internal cavities 46 and 48 by an integral, solid partition 50. Upper cavity 46 is open at the top 52, and lower cavity 48 is open at the bottom 54. As is clear in FIG. 4, upper cavity 46 is much smaller than lower cavity 48. Upper cavity 46 has both internal threads 56 and external threads 58 whereas lower cavity 48 has only external threads 60; see FIG. 2. Internal threads 34 of upper cap 16 threadedly mate with external threads 58 of body 20, and internal threads 42 of lower cap 22 threadedly mate with external threads 60 of body 20.

Turning to FIGS. 6–9 toothbrush 62 will be described. Toothbrush 62 comprises a toothbrush stem 64, bristles 66, and a base 68. Stem 64 and bristles 66 are conventional and can be any of the known toothbrush designs.

Figure 8:
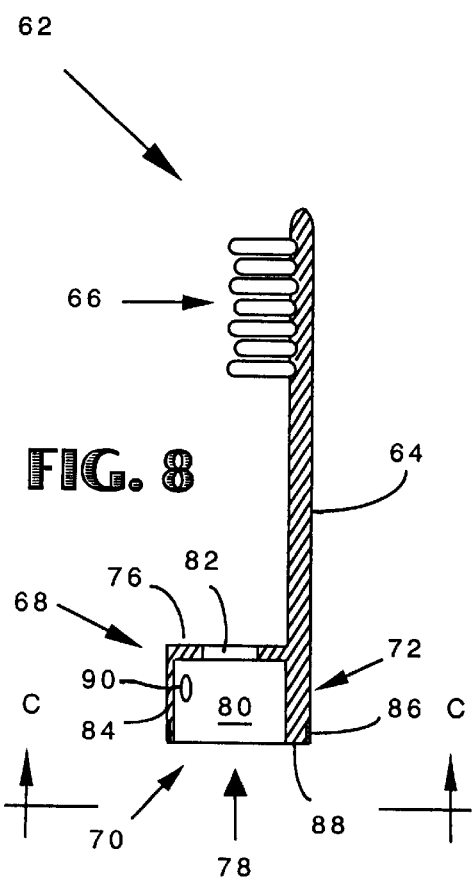
FIG. 8 is a cross-sectional side view of the toothbrush of FIG. 6 as seen along lines B—B of FIG. 7.
Figure 9:
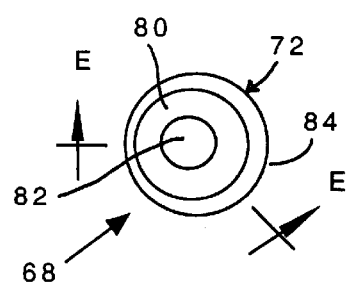
FIG. 9 is a bottom view of the toothbrush of FIG. 6 as seen along lines C—C of FIG. 8.

Base 68 is in the shape of an inverted cup 70 comprising a cylinder 72 (FIG. 8) covered at the top end 74 by an integral transverse wall 76 and open at the bottom end 78, thereby defining an interior, cylindrical receptacle 80. Wall 76 includes a circular aperture 82 therethrough. Stem 64 is shown as substantially oval in cross-section (FIG. 7), but obviously, it can take any shape. Stem 64 is integrally attached to wall 76 substantially tangent with the circumferential surface 84 of cylinder 72. Bristles 66 extend centrally over wall 76. This combination reduces the transverse dimensions, thereby reducing the transverse diameter of upper cap 16 and concomitantly the diameter of fountain pen 14. As can be seen in FIGS. 8–9, circular aperture 82 and cylindrical receptacle 80 are concentrically aligned, but both are off-set from circumferential surface 84, as most clearly seen in FIG. 9. In order to effect this arrangement, cylindrical wall 72 is preferably of variable thickness, gradually decreasing from its thickest portion beneath toothbrush stem 64 to its thinnest portion opposite thereof.

Figure 6:
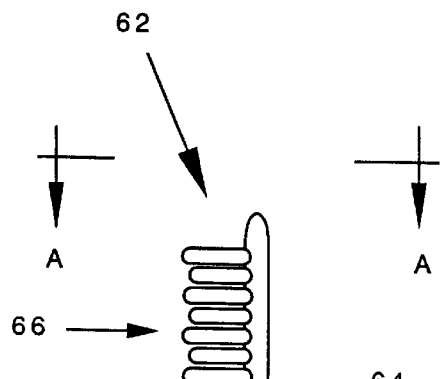
FIG. 6 is a side view of the toothbrush of the invention.
Figure 7:
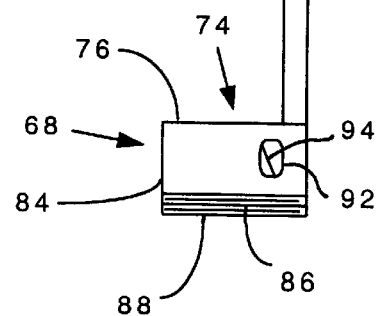
FIG. 7 is a top view of the toothbrush as seen along lines A—A of FIG. 6.

Cylinder 72 is externally threaded 86 adjacent the bottom edge 88. External threads 86 mate with internal threads 56 of body 20 (FIG. 4) to removably connect toothbrush 62 and body 20. Two apertures are located through cylinder 72, a smaller aperture 90 (FIG. 8) and a larger aperture 92 (FIG. 6). Aperture 92 includes a cutter 94 fixed across a portion thereof. Aperture 92 can be formed by striking cutter 94 outwardly from cylinder 72. The functional purposes of base 68 will be apparent shortly.

Figure 10:
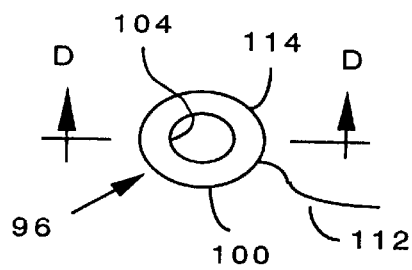
FIG. 10 is a top view of a spool of dental floss according to the invention.
Figure 11:
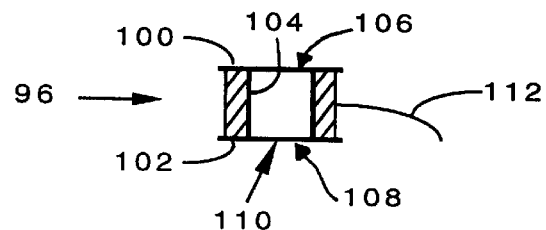
FIG. 11 is a cross-sectional side view of the spool of dental floss as seen along lines D—D of FIG. 10.

A top view of a spool 96 of dental floss 98 is shown in FIG. 10, and a cross-section thereof is shown in FIG. 11. Spool 96 comprises top and bottom circular flanges 100 and 102, respectively, integrally joined together by a connecting tube 104, thereby resembling a bobbin. Tube 104 is hollow and open at both top 106 and bottom 108 forming an open conduit 110 therethrough. Dental floss 98 is wound around tube 104, ending with an exposed bitter end 112.

Figure 12:
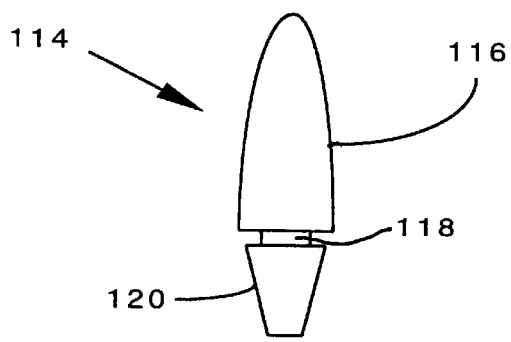
FIG. 12 is a perspective view of a tube of toothpaste according to the invention.

FIG. 12 displays a tube 114 of toothpaste (not shown). Tube 114 comprises a collapsible tube 116 with a neck 118 and a removable cap 120. A conventional miniature toothpaste tube is preferred, but a specially designed tube dimensioned to fit kit 10 is also contemplated for use.

Figure 13:
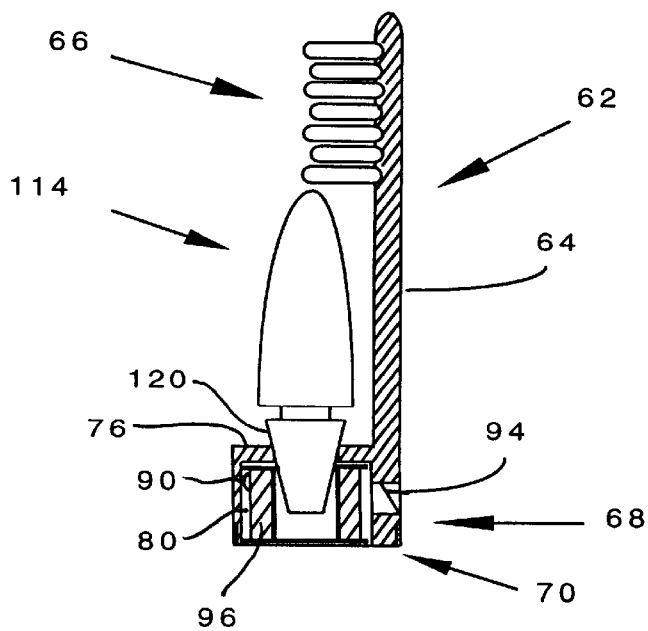
FIG. 13 is a side view, partially in cross-section as seen along lines E—E of FIG. 9, of the toothpaste and dental floss spool nested within the toothbrush.

Toothpaste tube 114 and dental floss spool 96 are designed to nest within toothbrush 62 in the manner shown in FIG. 13. Dental floss spool 96 is wholly but loosely fit within cylindrical receptacle 80 of cup 70 of base 68, snug enough to maintain its conformance with the interior of cylinder 72 without binding but loose enough to rotate easily as floss 98 is withdrawn therefrom. Bitter end 112 exits cylindrical wall 72 through smaller aperture 90 and is severed by contact with cutter 94. Cap 120 of tube 114 is inserted through aperture 82 of wall 76 of toothbrush 62 and into open conduit 110 of dental floss spool 96, where cap 120 acts as a stabilizing axle for spool 96, when floss 98 is being extracted therefrom. Cap 120 holds tube 114 upright and substantially parallel with toothbrush stem 64 between bristles 66 and transverse wall 76.

A canister 122 of breath spray 124 is shown in FIG. 14. Canister 122 includes a push-button valve 126, the depression of which releases the breath spray 124 to exit canister 122 as a mist as is conventional. Canister 122 has a cylindrical body 128 which is closed at its bottom 130.

FIG. 15 shows the storing of breath spray canister 122 within the larger cavity 48 of body 20. Canister 122 fits loosely within internal cavity 48 of body 20 with bottom 130 abutting transverse partition 50. A small portion of canister 122 and push-button valve 126 protrude from open bottom 54, thus permitting use of breath spray 124 without removing canister 122 from body 20. Lower cap 22 closes open bottom 54, when threads 42 and 60 are engaged, confining breath spray canister 122 within housing 12.

FIG. 16 shows oral hygiene kit 10 in its assembled state. Toothbrush 62, toothpaste tube 114, and dental floss spool 96 are nested together as shown in FIG. 13, and toothbrush 62 is threadedly connected to body 20 by coacting threads 56 and 86. In the preferred embodiment, both apertures 90 and 92 through base 68 are above body 20, when toothbrush 62 is threadedly connected to body 20, so dental floss 98 may be used without removing toothbrush 62 from body 20. And, access to both toothbrush 62 and dental floss 98 is gained by simply removing upper cap 16. It is within the purview of the invention, however, to extend threads 86 along a larger axial length of circumferential surface 84 of cylinder 72 and to provide a deeper, internally threaded cavity 46 with any degree of threading desired therebetween. Spool 96 is constrained within cavity 80 of base 68, where it is protected against becoming soiled, and is replaced by simply separating toothbrush 62 from body 20. When upper cap 16 is threadedly joined with body 20, toothbrush stem 64, bristles 66, and toothpaste tube 114 are concealed within hollow interior cavity 28 of upper cap 16. In this state, toothbrush 62 is protected against foreign contamination, and toothpaste tube 114 is protected against being accidentally crushed causing the toothpaste to foul the associated pocket, purse, or suitcase.

In use, when upper cap 16 and lower cap 22 are threaded onto body 20, the assemblage (FIG. 1) resembles a fountain pen 14 which is easily, unobtrusively carried in a pocket or purse. When needed, especially when away from home, upper cap 16 is removed from body 20, tube 114 is opened and toothpaste is applied to bristles 66. Body 20 acts as a handle for toothbrush 62 while brushing one's teeth. Should one wish to floss, bitter end 112 of dental floss 98 is conveniently exposed for use. To freshen one's breath, fountain pen 14 is inverted, and lower cap 22 is removed from body 20, exposing push-button valve 126 for use. When either the toothpaste or dental floss is exhausted, replacement thereof is easily accomplished without the necessity of laborious assembly.

It should be noted that each component of oral hygiene kit 10 is unitary with no moving parts, and they are connected simply by screwing the threaded parts together. Consequently, the manufacture of the components, namely, upper cap 16, body 20, lower cap 20, and toothbrush 62, are relatively inexpensive compared to prior fountain pen type oral hygiene kits.

It is clear from the above that the objects of the invention have been fulfilled. While the components of oral hygiene kit 10 are shown as having consistent dimensions in the various figures, the proportions shown are exaggerated for clarity. They are illustrative only and may be altered without notice. For instance, bristles 66 are shown shorter than desired (FIGS. 13, 16), in order to show the top of base 68 more clearly (FIG. 7); in practice, it is the extension of bristles 66 which determines the diameter of pen 14, which is contemplated as being narrower than depicted. In addition, breath spray canister 122 can be proportionally shorter than shown, and toothpaste tube 114 and toothbrush 62 can be longer. The disclosure is intended solely to teach the concepts of the invention to one skilled in the art and is not limiting of the scope of the invention which is the province of the appended claims.

Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention as defined in the appended claims.

Further, the purpose of the foregoing Abstract is to enable the U.S. Patent and Trademark Office, and the public generally, and especially the scientists, engineers and practitioners in the art who are not familiar with patent or legal terms or phraseology, to determine quickly from a cursory inspection the nature and essence of the technical disclosure of the application. The Abstract is neither intended to define the invention of the application nor is it intended to be limiting as to the scope of the invention in any way, which is measured solely by the following claims.

I claim as my invention:

1. An oral hygiene kit, comprising:
   a housing, said housing comprising a body, an upper cap, and a lower cap, said upper cap and lower cap being removably attached to said body;
   a toothbrush, said toothbrush comprising a base, a stem, and bristles, said base comprising a cylinder defining an interior, cylindrical receptacle which is open at one end and covered at the other end by a transverse wall, said transverse wall having an aperture therethrough;
   a spool of dental floss, said spool including a pair of flanges integrally connected by a cylindrical tube having an open conduit axially therethrough, said dental floss being wound about said cylindrical tube, and said spool of dental floss being wholly but loosely received within said cylindrical receptacle;
   a tube of toothpaste, said tube including a removable cap, said toothpaste tube being dimensioned to fit between said bristles and said transverse wall of said base with said toothpaste tube cap being inserted through said transverse wall aperture and into said cylindrical tube of said spool of dental floss; and
   said base being removably attached to said body and contained within said upper cap when said upper cap is attached to said body.

2. The oral hygiene kit of claim 1 wherein said body comprises a hollow cylinder separated into an upper internal cavity and a lower internal cavity by an integral, solid partition, said base and said upper cap being removably attached to said upper internal cavity and said lower cap being removably attached to said lower internal cavity.

3. The oral hygiene kit of claim 2 wherein said said upper internal cavity has an open end opposite said partition which is both internally and externally threaded, said lower internal cavity has an open end opposite said partition which is externally threaded, said base is externally threaded to mate with said internally threaded upper internal cavity and said upper cap is internally threaded to mate with said externally threaded upper internal cavity, and said lower cap is internally threaded to mate with said externally threaded lower internal cavity, whereby said upper and lower caps close said upper and lower internal cavities.

4. The oral hygiene kit of claim 3 further comprising a canister of breath spray, said breath spray canister being housed within said lower internal cavity and said lower cap, when said lower cap is threadedly attached to said lower internal cavity.

5. The oral hygiene kit of claim 4 wherein said canister includes a push-button valve which releases said breath spray when depressed, and said canister fits loosely within said lower internal cavity with a small portion of said canister and said push-button valve protruding from said lower internal cavity open end, thus permitting use of said breath spray without removing said canister from said lower internal cavity.

6. The oral hygiene kit of claim 5 further comprising a fountain pen type clasp attached to the exterior of said upper cap, wherein said housing resembles a fountain pen when said upper cap and lower cap are attached to said body.

7. An oral hygiene kit, comprising:
   a housing, said housing comprising a body, an upper cap, and a lower cap, said body comprising a hollow cylinder separated into an upper internal cavity and a lower internal cavity by an integral, solid partition, said upper cap comprising an internal cavity open at one end and closed at the other end and said lower cap comprising an internal cavity open at one end and closed at the other end, said upper cap and lower cap being removably attached to said body, and said housing resembling a fountain pen when said upper cap and lower cap are attached to said body;

a toothbrush, a tube of toothpaste, and a spool of dental floss, said toothbrush, said tube of toothpaste, and said spool of dental floss being housed within said upper internal cavity of said body and said internal cavity of said upper cap; and a canister of breath spray, said canister of breath spray being housed within said lower internal cavity of said body and said internal cavity of said lower cap.

8. The oral hygiene kit of claim 7 wherein said upper cap and lower cap are threadedly attached to said body.

9. The oral hygiene kit of claim 8 wherein said said upper internal cavity has an open end opposite said partition which is externally threaded, said lower internal cavity has an open end opposite said partition which is externally threaded, said upper cap is internally threaded to mate with said externally threaded upper internal cavity, and said lower cap is internally threaded to mate with said externally threaded lower internal cavity, whereby said upper and lower caps close said upper and lower internal cavities when threadedly attached thereto.

10. The oral hygiene kit of claim 9 further comprising a fountain pen type clasp attached to the exterior of said upper cap.

* * * * *